United States Patent
Vogel et al.

(10) Patent No.: US 7,687,676 B1
(45) Date of Patent: *Mar. 30, 2010

(54) DEHYDROGENATION PROCESS WITH WATER AND TEMPERATURE CONTROL

(75) Inventors: Christopher J. Vogel, Chicago, IL (US); Dean E. Rende, Arlington Heights, IL (US); Andrea G. Bozzano, Des Plaines, IL (US); Paul G. Wing, Wheaton, IL (US)

(73) Assignee: UOP LLC, Des Plaines, IL (US)

( * ) Notice: Subject to any disclaimer, the term of this patent is extended or adjusted under 35 U.S.C. 154(b) by 1078 days.

This patent is subject to a terminal disclaimer.

(21) Appl. No.: 11/357,534

(22) Filed: Feb. 17, 2006

Related U.S. Application Data

(60) Provisional application No. 60/654,243, filed on Feb. 18, 2005.

(51) Int. Cl.
*C07C 5/333* (2006.01)

(52) U.S. Cl. .............. 585/660; 585/374; 585/419; 585/434; 585/444; 585/624; 585/654; 260/683.3; 252/420; 208/138

(58) Field of Classification Search ........... 208/138; 252/420; 260/683.3; 585/374, 419, 434, 585/444, 624, 654, 660
See application file for complete search history.

(56) References Cited

U.S. PATENT DOCUMENTS

| | | | | |
|---|---|---|---|---|
| 3,907,921 | A | 9/1975 | Winter, III | 260/683.3 |
| 4,046,715 | A | 9/1977 | Wilhelm | 502/327 |
| 4,133,839 | A | 1/1979 | Hayes | 585/434 |
| 4,420,649 | A * | 12/1983 | Antos | 585/434 |
| 5,321,192 | A | 6/1994 | Cottrell et al. | 585/659 |
| 6,177,381 | B1 | 1/2001 | Jensen et al. | 502/325 |
| 6,417,422 | B1 | 7/2002 | Liu | 585/658 |
| 6,486,370 | B1 | 11/2002 | Rende et al. | 585/444 |
| 6,756,515 | B2 | 6/2004 | Rende et al. | 585/444 |

* cited by examiner

*Primary Examiner*—In Suk Bullock
*Assistant Examiner*—Prem C. Singh
(74) *Attorney, Agent, or Firm*—Arthur E Gooding

(57) ABSTRACT

The activity of a dehydrogenation catalyst is improved by increasing the water concentration maintained in the reactants toward the start of the catalyst's life, but after the catalyst has deactivated to the extent that the temperature required to maintain the conversion per pass of paraffinic hydrocarbon through the reaction zone increases by at least 2° C.

20 Claims, No Drawings

DEHYDROGENATION PROCESS WITH WATER AND TEMPERATURE CONTROL

CROSS-REFERENCE TO RELATED APPLICATION

This application claims priority from Provisional Application No. 60/654,243 filed Feb. 18, 2005, the contents of which are hereby incorporated by reference.

FIELD OF THE INVENTION

The invention relates to a process for the catalytic dehydrogenation of hydrocarbons.

BACKGROUND OF THE INVENTION

Processes for the catalytic dehydrogenation of hydrocarbons are well known. Paraffins having from 5 to 20 carbon atoms per molecule undergo such treatment to form the corresponding olefin. Olefins having from 9 to 16 carbon atoms per molecule are used to alkylate benzene to produce alkylbenzenes, which is an intermediate in the manufacture of detergents. Shorter chain olefins having 5 carbon atoms per molecule are used to alkylate isoparaffins or to etherify alcohols to make motor fuel blending components. A great many other uses for such olefins are known.

Many catalytic dehydrogenation processes use a reactor containing a bed of catalyst. The activity of the catalyst decreases in a gradual manner and the reactor inlet temperature is gradually increased to compensate for this. As this temperature rises, the rate of undesired side reactions will increase, and the selectivity of the process to the desired olefin will suffer. When the temperature rises to an upper limit (e.g., the design temperature of process equipment) or the selectivity of the process drops below a useful level (e.g., the minimum profitable selectivity), the effective life of the catalyst is reached, the "run" of the catalyst is completed, and the catalyst must be replaced.

The effective life of the catalyst typically is approximately inversely proportional to the conversion per pass at which the dehydrogenation process is operated. Operators of these processes select a value of conversion per pass of the feed hydrocarbon through the reactor to optimize operation of the process. This desired conversion per pass will vary with the objectives of the operator. The value may be preselected prior to the start of a run of dehydrogenation catalyst and then maintained throughout the run as the catalyst ages. Alternatively, the value may be varied during the run as the catalyst ages. A process can be operated at a number of different conversions per pass as the catalyst ages and the temperature required to maintain the initial preselected conversion per pass increases. The most important factors in determining the desired conversion per pass are the temperature required to maintain a given conversion per pass as the catalyst ages and the selectivity of the process at a given conversion per pass. The temperature required in a dehydrogenation process to maintain a given conversion per pass depends on the conversion per pass, the composition and condition of the catalyst, the reactants, and other dehydrogenation conditions.

Dehydrogenation processes and catalysts have previously been found to be affected by the presence of water, as described in U.S. Pat. Nos. 3,448,165 (Bloch); 3,907,921 (Winter, III); 5,321,192 (Cottrell et al.); 6,177,381 (Jensen et al.); 6,486,370 B1 (Rende et al.); and 6,756,515 B2 (Rende et al.). U.S. Pat. No. 3,907,921, for example, describes injecting water at an initially optimum value and then increasing the water concentration in the reactant stream as the catalyst becomes less active. U.S. Pat. No. 6,756,515 B2 describes a dehydrogenation process wherein water at less than 1000 wt-ppm based on the hydrocarbon weight is passed to a layered composition in order to decrease the catalyst deactivation rate.

Processes for dehydrogenating hydrocarbons with improved effective catalyst lives and decreased temperatures at a given conversion per pass are sought.

SUMMARY OF THE INVENTION

The process disclosed herein is for catalytically dehydrogenating hydrocarbons using a very low concentration of or essentially no water or water precursors in the combined feed to a reactor when the dehydrogenation catalyst is fresh, and then increasing the concentration of water, water precursor, or both as the catalyst becomes less active or the conversion per pass declines. The benefits of this process can include increased catalyst life, reduced reactor inlet temperature for a given conversion per pass of the dehydrogenatable hydrocarbons, or improved selectivity. The catalysts used in the process contain a platinum group component and a promoter component supported on a carrier material. The process is particularly useful for layered catalyst compositions and surface-impregnated catalysts.

The water, water precursors, or both is increased after the conversion per pass has decreased by at least 0.1 molar percentage points. In one embodiment, the water, water precursors, or both is increased after the temperature required to maintain a preselected conversion per pass of paraffinic hydrocarbon through the reactor exceeds the initial temperature required to achieve the preselected conversion per pass by at least 2° C. (4° F.). In another embodiment, the water, water precursors, or both is increased while maintaining the temperature substantially constant.

INFORMATION DISCLOSURE

U.S. Pat. No. 3,907,921 (Winter III) describes a dehydrogenation process characterized by initially injecting 5 to 25 wt-ppm water into the feed stream, and then increasing the rate of water injection to 25 to 125 wt-ppm after at least 40% of the normal paraffins which may be processed before the catalyst requires replacement have passed through the reaction zone.

U.S. Pat. No. 5,321,192 (Cottrell et al.) describes a dehydrogenation process characterized by introducing a relatively small amount of water or water precursor at the inlet of two or more catalytic dehydrogenation zones.

U.S. Pat. No. 6,177,381 (Jensen et al.) describes a dehydrogenation process using a layered catalyst composition and includes test results of several catalysts for dehydrogenation activity using a hydrocarbon feed and injecting a water concentration of 2000 wt-ppm based on the hydrocarbon weight.

U.S. Pat. Nos. 6,486,370 B1 (Rende et al.) and 6,756,515 B2 (Rende et al.) describe a dehydrogenation process characterized by using a layered catalyst composition and dehydrogenation conditions comprising adding water to the dehydrogenation zone to provide less than 2000 wt-ppm and less than 1000 wt-ppm, respectively, of the hydrocarbon feed stream. Both patents describe providing water at possibly even less than 1 wt-ppm of the hydrocarbon feed stream.

DETAILED DESCRIPTION

Hydrocarbons having from 5 to 20, and preferably 8 to 16, carbon atoms can be dehydrogenated in the process disclosed herein. These hydrocarbons include normal paraffins, isoparaffins including monomethyl paraffins and dimethyl paraffins, alkylaromatics, naphthenes, and olefins, either alone or in a mixture thereof.

A suitable arrangement for the dehydrogenation process disclosed herein is described, for instance, in U.S. Pat. No. 6,670,516 B1, herein incorporated in its entirety by reference. Fresh hydrocarbon feed combines with hydrogen, which may be provided in a hydrogen-containing gaseous recycle stream. This forms a reactant stream which is called a combined feed. Recycled unconverted hydrocarbons may also be a component of the combined feed. The combined feed is passed through a bed of suitable catalyst maintained at the proper dehydrogenation conditions such as temperature, pressure and space velocity. The effluent from the catalytic reaction zone is passed to a separation zone wherein the effluent is cooled and partially condensed.

At least a portion of the uncondensed material is recycled as the gaseous recycle stream comprising hydrogen and light hydrocarbon gases. The net hydrogen which is produced in the process is vented for use in other applications such as desulfurization. The separation zone produces a liquid stream containing the dehydrogenated and undehydrogenated hydrocarbons. The liquid stream is then separated to recover the dehydrogenated hydrocarbons from the unconverted hydrocarbons which may then be recycled. This separation is done by passing the liquid stream into a stripping column to remove dissolved gases and cracked light ends. The liquid stream which has been treated in the stripping column is then separated to recover the dehydrogenated hydrocarbons.

When paraffins are being processed, the olefins may be alkylated with benzene to produce detergent intermediates such as alkylbenzenes. The practice in this situation is to pass the liquid stream from the stripping column into the detergent alkylation process. However, the liquid stream may contain diolefinic and aromatic byproducts formed during dehydrogenation which can adversely affect the quality of the detergent. Therefore, the liquid stream may be optionally further treated before entering the detergent alkylation process to selectively hydrogenate diolefins to the corresponding monoolefin and to selectively remove aromatics.

The paraffins used to make the olefins for detergent intermediates may vary widely and may be branched, linear or slightly branched acyclic paraffins of from about 9 to about 19, often 9 to 14, carbon atoms per molecule, and are often present as a mixture of paraffins. Due to environmental concerns, where the alkylbenzenes are intended to be sulfonated to make detergents, the paraffins are linear (making linear alkylbenzenes (LAB's) or slightly branched (making modified alkylbenzenes (MAB's)). During dehydrogenation, skeletal isomerization of the paraffin is minimal, and the resulting olefin has usually the same hydrocarbon backbone and extent of branching as the paraffin. The resulting olefin is usually monoolefinic, and the positioning of the olefinic bond in the molecule is not critical. However, the branching of the hydrocarbon backbone is often more of a concern as the structural configuration of the alkyl group on the alkylbenzene product can affect performance. For instance, where alkylbenzenes are sulfonated to produce detergents, undue branching can adversely affect the biodegradability of the detergent. On the other hand, some branching may be desired such as the lightly branched modified alkylbenzenes such as described in U.S. Pat. No. 6,187,981 B1, herein incorporated in its entirety by reference. The paraffin may be unbranched or lightly branched, which as used herein, refers to a paraffin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms.

The process disclosed herein uses a catalyst that comprises a platinum group component and a promoter component on a carrier material. Preferably, the catalyst also comprises a modifier component, a halogen component, or both.

The carrier material used in the process disclosed herein may be formed in any desired shape such as spheres, pills, cakes, extrudates, powders, granules, etc. and it may be used in any particle size. A preferred form of carrier material is the sphere. A preferred range of particle diameters is about 0.50 to about 2.00 mm (0.020 to 0.079 in). Preferred particle diameters are about 1.59 mm (1/16 in) and about 0.79 mm (1/32 in). Other preferred forms include cylinders, polylobular shapes having 2, 3 or up to about 8 lobes, and shapes having one or more open channels such as a tubular or cartwheel particle. See U.S. Pat. Nos. 4,652,687 and 4,717,781. The carrier material can be prepared in any suitable manner from synthetically prepared or naturally occurring materials.

The catalyst used in the process disclosed herein can comprise a layered composition. The layered composition comprises an inner core composed of a material which has substantially lower adsorptive capacity for catalytic metal precursors, relative to the outer layer. Some of the inner core materials are also not substantially penetrated by liquids, e.g., metals including but not limited to aluminum, titanium and zirconium. Examples of the inner core material include, but are not limited to, refractory inorganic oxides, silicon carbide and metals. Examples of refractory inorganic oxides include without limitation alpha alumina, theta alumina, cordierite, zirconia, titania and mixtures thereof. A preferred inorganic oxide is alpha alumina.

These materials which form the inner core can be formed into a variety of shapes such as pellets, extrudates, spheres or irregularly shaped particles although not all materials can be formed into each shape. Preparation of the inner core can be done by means known in the art such as oil dropping, pressure molding, metal forming, pelletizing, granulation, extrusion, rolling methods and marumerizing. A spherical inner core is preferred. The inner core whether spherical or not has an effective diameter of about 0.05 mm to about 5 mm (0.002 to 0.2 in) and preferably from about 0.8 mm to about 3 mm (0.03 to 0.12 in). For a non-spherical inner core, effective diameter is defined as the diameter the shaped article would have if it were molded into a sphere. Once the inner core is prepared, it is calcined at a temperature of about 400 to about 1500° C. (752 to 2732° F.).

The inner core is now coated with a layer of a refractory inorganic oxide which is different from the inorganic oxide which may be used as the inner core and is referred to herein as the outer refractory inorganic oxide. This outer refractory inorganic oxide is one which has porosity, has a surface area of at least 50 $m^2/g$, and preferably at least 150 $m^2/g$, an apparent bulk density of about 0.2 g/ml, and is chosen from the group consisting of (1) gamma alumina, delta alumina, eta alumina, theta alumina, titania, zirconia, and silica-alumina; (2) zeolites such as naturally occurring or synthetically prepared zeolite Y, zeolite X, zeolite L, zeolite beta, ferrierite, MFI, mordenite, erionite, faujasite, silicalite, or other zeolites, either in the hydrogen form or in a form that has been exchanged with metal cations; (3) non-zeolitic molecular sieves (NZMS) such as the SAPOs, ELAPOs, and MeAPOs. Preferred outer refractory inorganic oxides are gamma and eta alumina.

A preferred way of preparing a gamma alumina is by the well-known oil drop method which is described in U.S. Pat. No. 2,620,314, herein incorporated in its entirety by reference. The oil drop method comprises forming an aluminum hydrosol by any of the techniques taught in the art and preferably by reacting aluminum metal with hydrochloric acid; combining the hydrosol with a suitable gelling agent, e.g., hexamethylenetetraamine; and dropping the resultant mixture into an oil bath maintained at elevated temperatures (about 93° C. (199° F.)). The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged and gelled spheres are then washed and dried at a relatively low temperature of about 80 to 260° C. (176 to 500° F.) and then calcined at a temperature of about 455 to 705° C. (851 to 1301° F.) for a period of about 1 to about 20 hours. This treatment effects conversion of the hydrogel to the corresponding crystalline gamma alumina.

The layer is applied by forming a slurry of the outer refractory inorganic oxide and then coating the inner core with the slurry by means well known in the art. Slurries of inorganic oxides can be prepared by means well known in the art which usually involve the use of a peptizing agent. For example, any of the transitional aluminas can be mixed with water and an acid such as nitric, hydrochloric, or sulfuric to give a slurry. Alternatively, an aluminum sol can be made by for example, dissolving aluminum metal in hydrochloric acid and then mixing the aluminum sol with the alumina powder.

The slurry may contain an organic bonding agent which aids in the adhesion of the outer refractory inorganic oxide layer to the inner core. Examples of this organic bonding agent include but are not limited to polyvinyl alcohol (PVA), hydroxy propyl cellulose, methyl cellulose and carboxy methyl cellulose. The amount of organic bonding agent which is added to the slurry will vary considerably from about 0.1 wt-% to about 3 wt-% of the slurry. How strongly the outer layer is bonded to the inner core can be measured by the amount of layer material lost during an attrition test, i.e., attrition loss. Loss of the outer layer by attrition is measured by agitating the catalyst, collecting the fines and calculating an attrition loss. It has been found that by using an organic bonding agent as described above, the attrition loss is less than about 10 wt-% of the outer layer. Finally, the thickness of the outer layer varies from about 40 to about 150 microns. One micron equals $10^{-6}$ meter.

Depending on the particle size of the outer refractory inorganic oxide, it may be necessary to mill the slurry in order to reduce the particle size and simultaneously give a narrower particle size distribution. This can be done by means known in the art such as ball milling for times of about 30 minutes to about 5 hours and preferably from about 1.5 to about 3 hours. It has been found that using a slurry with a narrow particle size distribution improves the bonding of the outer layer to the inner core.

The slurry may also contain an inorganic bonding agent selected from an alumina bonding agent, a silica bonding agent or mixtures thereof. Examples of silica bonding agents include silica sol and silica gel, while examples of alumina bonding agents include alumina sol, boehmite and aluminum nitrate. The inorganic bonding agents are converted to alumina or silica in the finished composition. The amount of inorganic bonding agent varies from about 2 to about 15 wt-% as the oxide, and based on the weight of the slurry.

Coating of the inner core with the slurry can be accomplished by means such as rolling, dipping, spraying, etc. One preferred technique involves using a fixed fluidized bed of inner core particles and spraying the slurry into the bed to coat the particles evenly. The thickness of the layer can vary considerably, but usually is from about 40 to about 150 microns. The optimum layer thickness depends on the choice of the outer refractory inorganic oxide. Once the inner core is coated with the layer of outer refractory inorganic oxide, the resultant layered support is dried at a temperature of about 100 to about 320° C. (212 to 608° F.) for a time of about 1 to about 24 hours and then calcined at a temperature of about 400 to about 900° C. (752 to 1652° F.) for a time of about 0.5 to about 10 hours to effectively bond the outer layer to the inner core and provide a layered catalyst support. Of course, the drying and calcining steps can be combined into one step.

When the inner core is composed of a refractory inorganic oxide (inner refractory inorganic oxide), preferably the outer refractory inorganic oxide be different from the inner refractory inorganic oxide. Additionally, it is preferably that the inner refractory inorganic oxide have a substantially lower adsorptive capacity for catalytic metal precursors relative to the porous carrier material.

Having obtained the layered carrier material, the platinum group component, promoter component, and optional modifier component can be dispersed on the layered carrier material by means known in the art. Thus, these three components can be dispersed on the outer layer. The platinum group component may be selected from the group consisting of platinum, palladium, iridium, rhodium, osmium, ruthenium, and mixtures thereof. Platinum, however, is the preferred platinum group component. The promoter component may be selected from the group consisting of tin, germanium, rhenium, gallium, bismuth, lead, indium, cerium, zinc, and mixtures thereof. The preferred promoter component is tin. The modifier component may be selected from the group consisting of alkali metals (IUPAC Group 1), alkaline earth metals (IUPAC Group 2), and mixtures thereof. All references herein to groups of elements are to the Periodic Table of the Elements, "CRC Handbook of Chemistry and Physics," CRC Press, Boca Raton, Fla., $80^{th}$ Edition, 1999-2000. The alkali and alkaline earth metals which can be used as modifier components on the catalyst used in the process disclosed herein include lithium, sodium, potassium, cesium, rubidium, beryllium, magnesium, calcium, strontium and barium. Most commonly used modifier metals are lithium, potassium, sodium and cesium.

The platinum group component, promoter component, and optional modifier component can be deposited on the layered carrier material in any suitable manner known in the art. One method involves impregnating the layered carrier material with a solution (preferably aqueous) of a decomposable compound of the metal or metals. By decomposable it is meant that upon heating the metal compound is converted to the metal or metal oxide with the release of byproducts. Illustrative of the decomposable compounds of the platinum group component are chloroplatinic acid, ammonium chloroplatinate, bromoplatinic acid, dinitrodiamino platinum, sodium tetranitroplatinate, rhodium trichloride, hexa-aminerhodium chloride, rhodium carbonylchloride, sodium hexanitrorhodate, chloropalladic acid, palladium chloride, palladium nitrate, diaminepalladium hydroxide, tetraaminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexa-amineruthenium chloride, osmium trichloride and ammonium osmium chloride. Illustrative of the decomposable promoter component compounds are the halide salts of the promoter components. A preferred promoter component is tin and preferred decomposable compounds are stannous chloride or stannic chloride. Illustrative of the decomposable compounds of the optional modifier component are the halide, nitrate, carbonate or hydroxide compounds of the alkali and alkaline earth metals, e.g., potassium hydroxide, lithium nitrate.

The platinum group component, promoter component, and optional modifier component can be impregnated using one common solution or they can be sequentially impregnated in any order, but not necessarily with equivalent results. A preferred impregnation procedure involves the use of a steam-jacketed rotary dryer. The support is immersed in the impregnating solution containing the desired metal compound contained in the dryer and the support is tumbled therein by the rotating motion of the dryer. Evaporation of the solution in contact with the tumbling support is expedited by applying steam to the dryer jacket. The resultant composite is allowed to dry under ambient temperature conditions, or dried at a temperature of about 80 to about 350° C. (176 to 662° F.), followed by calcination at a temperature of about 200 to about 700° C. (392 to 1292° F.) for a time of about 1 to about 4 hours, thereby converting the component to the metal or metal oxide. For the platinum group component, the preferred calcination temperature is about 400 to about 700° C. (752 to 1292° F.).

In one method of preparation, the promoter component is first deposited onto the layered carrier material and calcined as described above and then the modifier component and platinum group component are simultaneously dispersed onto the layered support by using an aqueous solution which contains a compound of the modifier component and a compound of the platinum group component. The support is impregnated with the solution as described above and then calcined at a temperature of about 400 to about 700° C. (752 to 1292° F.) for a time of about 1 to about 4 hours.

An alternative method of preparation involves adding one or more of the components to the outer refractory inorganic oxide prior to applying it as a layer onto the inner core. For example, a decomposable salt of the promoter component, e.g., tin (IV) chloride, can be added to a slurry composed of gamma alumina and aluminum sol. Further, either the modifier component or the platinum group component or both can also be added to the slurry before the slurry is applied to the inner core. Thus, in one method, all three catalytic components are deposited onto the outer refractory inorganic oxide prior to depositing the outer refractory inorganic oxide onto the inner core. Again, the three catalytic components can be deposited onto the outer refractory inorganic oxide powder in any order although not necessarily with equivalent results.

Another method of preparation involves first impregnating the promoter component onto the outer refractory inorganic oxide and calcining as described above. Next, a slurry is prepared (as described above) using the outer refractory inorganic oxide containing the promoter component and applied to the inner core by means described above. Finally, the platinum group component and the modifier component are simultaneously impregnated onto the layered composition and calcined as described above to give the desired layered catalyst.

As a final step in the preparation of the layered catalyst composition, the catalyst composition is reduced under hydrogen or other reducing atmosphere. Reduction is carried out at a temperature of about 100 to about 650° C. (212 to 1202° F.) for a time of about 0.5 to about 10 hours in a reducing environment, preferably dry hydrogen. The reduction conditions ensure that at least 90% and more preferably at least 95% of the platinum group component exists within the final catalytic composite in the metallic state (zero valent). The platinum group component may be combined with other catalyst components. For example, the platinum group component may be present in the form of an alloy with the promoter component, such as a platinum-tin alloy. However, the reduction conditions are such that more than 50% and preferably more than 75% of the promoter component is present in an oxidation state above that of the elemental metal, that is, in the +2 or +4 oxidation state in the case of tin, as a chemical compound such as the oxide, for example, and combined with the carrier material or with the platinum group component. The modifier component is mainly present in an oxidation state above that of the elemental metal. The modifier component may be present as a compound such as the oxide, for example, or combined with the carrier material or with the other components. The state of the promoter component and modifier component can be metallic (zero valent), metal oxide or metal oxychloride.

The layered catalyst composition can also contain a halogen component which can be fluorine, chlorine, bromine, iodine or mixtures thereof with chlorine and bromine preferred. This halogen component is present in an amount of 0.03 to about 1.5 wt-% with respect to the weight of the entire catalyst composition. The halogen component can be applied by means well known in the art and can be done at any point during the preparation of the catalyst composition although not necessarily with equivalent results. It is preferred to add the halogen component after all the catalytic components have been added either before or after treatment with hydrogen. The halogen component is generally present in a combined state with the carrier material.

Although all three metals are uniformly distributed throughout the outer layer of outer refractory oxide and substantially present only in the outer layer, it is also within the bounds of the process disclosed herein that the modifier component can be present both in the outer layer and the inner core. This is owing to the fact that the modifier component can migrate to the inner core, when the core is other than a metallic core.

Although the concentration of each component can vary substantially, it is desirable that the platinum group component be present in a concentration of about 0.01 to about 5 weight percent on an elemental basis of the entire weight of the catalyst and preferably from about 0.05 to about 2.0 wt-%. The promoter component is present in an amount from about 0.05 to about 10 wt-% of the entire catalyst while the modifier component is present in an amount from about 0.1 to about 5 wt-% of the entire catalyst. Finally, the atomic ratio of the platinum group component to promoter component varies from about 0.05 to about 5. In particular when the promoter component is tin, the atomic ratio is from about 0.1:1 to about 5:1 and preferably from about 0.5:1 to about 3:1. When the promoter component is germanium the ratio is from about 0.25:1 to about 5:1 and when the promoter component is rhenium, the ratio is from about 0.05:1 to about 2.75:1.

The preferred layered catalyst disclosed herein has a preferred concentration of the platinum group component in the outer layer. This concentration is generally from about 0.026 to about 0.26 gram-mole of the platinum group component, on an elemental basis per kilogram of the outer layer. When the platinum group component is platinum, this concentration is from about 0.5 to about 5 wt-% of platinum on an elemental basis and based on the weight of the outer layer. For a given concentration of the platinum group component in the outer layer, there is a preferred atomic ratio of the platinum group component to the promoter component. For example, when the platinum concentration is between about 0.5 and about 3 wt-% of platinum on an elemental basis and based on the weight of the outer layer, the preferred atomic ratio of platinum to tin is from between about 0.6:1 to about 1.3:1, increasing as the platinum concentration increases.

Suitable catalysts generally have a loading of the platinum group component of from about 5 to about 30 gram-mole of the platinum group component on an elemental basis per cubic meter of the layered catalyst. When the platinum group component is platinum, this loading is from about 0.0010 to about 0.0060 gram of platinum on an elemental basis per cubic centimeter of catalyst.

The concentration of the platinum group component in the outer layer can be readily determined in at least three ways. First, the concentration can be computed based on the weight of the ingredients used in preparing the layered catalyst. Second, in the case where the layered catalyst has previously been prepared and the inner refractory inorganic oxide is different from the outer refractory inorganic oxide, then the inner layer refractory inorganic oxide can be separated from the outer refractory inorganic oxide, and the platinum group metal can be separately recovered, by known chemical and/or mechanical methods. Then, the concentration of the weight of the platinum group component can be determined from the weight of recovered platinum group component and the weight of recovered inner refractory inorganic oxide. Finally, energy dispersive x-ray spectroscopy or wavelength dispersive spectroscopy (EPMA) using a scanning electron microscope of a sample of the layered catalyst may also be used.

Another embodiment of the process disclosed herein uses a catalytic composite comprising a platinum group component and a promoter component, and the platinum group component, and optionally the promoter component, are surface-impregnated upon the catalytic composite. The platinum group component is selected from the components disclosed and taught hereinabove as suitable for the platinum group component in another embodiment of the process disclosed herein. The promoter component is selected from the components disclosed and taught hereinabove as suitable for the promoter component in another embodiment of the process disclosed herein.

A component can be surface-impregnated upon the catalytic composite by any means suitable or any known technique which achieves the necessary distribution of components as described herein. One method for the surface impregnation of the components on a dehydrogenation catalyst is to adjust the pH of the impregnation solution to control the location of the components. Another method for the surface impregnation is to restrict the total volume of the impregnation solution in order to restrict the penetration of solution and thereby components into the support particle. Further information on surface impregnation is in U.S. Pat. Nos. 4,716,143; 4,880,764; 4,973,779; and 5,012,027.

Both the platinum group and promoter components are located on a carrier material having a nominal diameter (d) of from 50 to 10000 microns, where d is the nominal diameter of the catalyst particle in microns. In one aspect of this embodiment, a component is considered to be surface-impregnated upon the catalytic composite when the average concentration of the component within the 0.2 d micron exterior layer of the catalytic composite is at least two times the average concentration of the component in the 0.4 d micron diameter center core of the catalyst particle. It is to be understood that the term "exterior" is defined as the outermost layer of the catalytic composite. By "layer" it is meant a stratum of substantially uniform thickness. By "0.2 d" and "0.4 d", it is meant that the nominal diameter (d) is multiplied by 0.2 or 0.4. In another aspect of this embodiment, a component is considered to be surface-impregnated upon the catalytic composite when the average concentration of the component within the exterior 5 to 200 micron layer of the catalytic composite is at least two times the average concentration of the component in the 200 micron diameter center core of the catalyst particle. In this aspect, the exterior layer of the catalytic composite is preferably from 25 to 150 microns in thickness. In a third aspect of this embodiment, a component is considered to be surface-impregnated on the catalytic composite when substantially all of the component is located within at most a 400 micron exterior layer of the catalytic composite. By "substantially all" it is meant that at least about 75% of the surface-impregnated component in question.

Alternatively, where the catalytic composite has a nominal diameter of at least 850 micron, the surface-impregnated component may be described as being on average at least twice as concentrated in the outer 100 micron layer exterior layer of the catalytic composite in comparison to the average concentration of the surface-impregnated component in the 200 micron center core of the catalyst particle. The exterior layer wherein 75% of the surface-impregnated component is located will approach 100 microns. The exterior layer wherein 75% of the surface-impregnated component is located will approach a maximum value of 400 microns as the diameter of the catalyst support increases beyond 2000 microns.

This characterization of the catalytic composite is intended to describe a platinum group component concentration and an optionally surface-impregnated promoter component concentration gradient upon and within the catalytic composite. The platinum group component concentration, and optionally the promoter component concentration, tapers off from the exterior layer as the center of the catalytic composite is approached. The actual gradient of the platinum group component and optionally the promoter component within the catalytic composite varies depending upon the exact manufacturing method employed to fabricate the catalytic composite.

Although it is not understood completely, it is believed that by concentrating the surface-impregnated components to an exterior layer of the catalyst support, more facile and selective access to these catalytic sites is achieved, allowing the hydrocarbon reactions and products much shorter diffusion paths. By decreasing the length of the diffusion paths the reactants and products have a shorter residence time in the catalyst particle thereby lessening the likelihood of undesirable side reaction due to secondary reactions. This results in an increase in selectivity to the desired product. For example, in the dehydrogenation of the paraffin to a monoolefin, reducing the length of the diffusion path decreases the chances of dehydrogenating the desired monoolefin consecutively to undesirable skeletal isomers, cracked products, and aromatics by their readsorption onto a catalytic site before they can exit the catalyst particle.

The carrier material for the surface-impregnated catalytic composite may be selected from the inorganic oxides disclosed and taught hereinabove as suitable for the outer refractory inorganic oxide in another embodiment of the process disclosed herein. In addition, the carrier material may be (1) activated carbon, coke, or charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) other refractory inorganic oxides such as chromium oxide, beryllium oxide, vanadium oxide, cesium oxide, hafnium oxide, zinc oxide, magnesia, boria, thoria, silica-magnesia, chromia-alumina, alumina-boria, silica-zirconia, etc.; (5) spinels such as $MgAl_2O_4$, $FeAl_2O_4$, $ZnAl_2O_4$, $CaAl_2O_4$, and other like compounds having the formula $MO—Al_2O_3$ where M is a metal having a valence of 2; and (6) combinations of materials from one or more of these groups and the inorganic oxides disclosed and taught hereinabove as suitable for the outer refractory inorganic oxide. Preferred inorganic oxides for this embodiment of the process disclosed herein are gamma and eta alumina. In this embodiment, a modifier component, a halogen component, or both, may be incorporated into the catalytic composite by any known technique. Optionally, the catalytic composite used in this embodiment of the process disclosed herein can also contain a sulfur component. Generally, the sulfur component will comprise about 0.01 to about 1.0 wt-%, calculated on an elemental basis, of the final catalytic composite. The sulfur component may be incorporated into the catalytic composite in any suitable manner. Preferably sulfur or a compound containing sulfur such as hydrogen sulfide or a lower molecular weight mercaptan, for example, is contacted with the catalytic composite in the presence of hydrogen at a hydrogen to sulfur ratio of about 10 and a temperature of from about 10 to about 540° C. (50 to 1004° F.), preferably under water-free conditions, to incorporate the sulfur component.

After the components have been surface-impregnated or otherwise incorporated, the resultant composite is allowed to dry under ambient temperature conditions, or dried at a temperature of from about 80 to about 350° C. (176 to 662° F.), followed by calcination at a temperature of about 200 to about 700° C. (392 to 1292° F.) for a time of about 1 to about 4 hours, thereby converting the component to the metal or metal oxide. For the platinum group component, the preferred calcination temperature is about 400 to about 700° C. (752 to 1292° F.). As a final step in the preparation of the surface-impregnated catalytic composite used in this embodiment of the process disclosed herein, the catalytic composite is reduced under hydrogen or other reducing atmosphere, in the manner described for another embodiment of the process disclosed herein.

A third embodiment of the process disclosed herein uses a catalytic composite comprising a platinum group component and a promoter component, and the platinum group component and the promoter component are uniformly distributed upon the catalytic composite. The platinum group and promoter components are selected from those disclosed and taught hereinabove as suitable for these respective components in another embodiment of the process disclosed herein. A component can be uniformly distributed upon the catalytic composite by any means suitable or any known technique which achieves the a uniform distribution of components. Further information on preparing such a catalytic composite, including the optional incorporation of a modifier component, halogen component, a sulfur component, or any combination thereof, is in U.S. Pat. No. 4,486,547.

This detailed discussion of preferred dehydrogenation catalysts is not intended to limit the scope of the process disclosed herein. The great difficulty of accurately predicting which catalytic materials are beneficially affected by increased water addition precludes a complete listing of those compositions to which the process disclosed herein applies. It is envisioned that the process disclosed herein could be applied to other catalysts such as those containing osmium, iridium, or indium in addition to or in place of the promoter component of the preferred catalyst.

Although it is not understood completely, it is believed that the catalyst used in the process disclosed herein can deactivate according to two different mechanisms depending in part on the presence of water during the dehydrogenation reactions. One mechanism, which is believed to be based on coke formation, predominates at the beginning of a run when there is little or no water present. A second mechanism, which is believed to be based on interaction between the platinum group component (e.g., platinum) and the promoter component (e.g., tin), predominates once water is present. The introduction of a sufficient amount of water gives the catalyst an opportunity to deactivate by the second mechanism, despite having already deactivated somewhat by the first mechanism, and this extends the effective life of the catalyst. Neither the claims nor the process disclosed herein, however, is limited to any particular theory.

The effective life of the preferred dehydrogenation catalyst is approximately inversely proportional to the conversion per pass at which the process is operated. For example, at 2% conversion per pass the catalyst shows only a minimal rate of deactivation. At 10% conversion per pass the deactivation rate is higher and the useful life of a typical commercial catalyst is less, and at about 13% conversion per pass the commercially useful life is even shorter. The term "conversion per pass" as used herein is computed by subtracting the moles of undehydrogenated hydrocarbons in the reaction zone effluent from the moles of dehydrogenatable hydrocarbons in the reaction zone feed, then dividing by the moles of dehydrogenatable hydrocarbons in the reaction zone feed, and finally multiplying by 100. For example, if the dehydrogenatable hydrocarbons are $C_9$-$C_{13}$ paraffins, conversion per pass is computed by subtracting the moles of $C_9$-$C_{13}$ paraffins in the reaction zone effluent from the moles of $C_9$-$C_{13}$ paraffins in the reaction zone feed, then dividing by the moles of $C_9$-$C_{13}$ paraffins in the reaction zone feed, and finally multiplying by 100. The process disclosed herein is typically practiced at a conversion per pass in the range of from about 8 to about 20%, although the conversion per pass may be below or above this range.

The term "preselected conversion per pass" as used herein is intended to refer to a value of conversion per pass selected by the operator of a dehydrogenation process to optimize operation of the process. This desired conversion per pass will vary with the objectives of the operator. The value may be preselected prior to the start of a "run" of dehydrogenation catalyst and then maintained substantially constant throughout the run as the catalyst ages. Alternatively, the value may be varied during the "run" as the catalyst ages. For example, the conversion per pass of the reactants through the catalyst bed may be preselected at 12 or 15% at the start of the run and 9 or 11% at the end of the run. It may be desirable to operate the process to obtain a number of different preselected conversions per pass as the catalyst ages and the temperature required to maintain the initial preselected conversion per pass increases. For the dehydrogenation catalysts described above, operating at a conversion per pass of from about 8 to about 20 weight percent of the paraffinic hydrocarbon passed to the reaction zone, the initial required temperature for fresh catalyst at start-of-run is in the range of from about 450 to about 485° C. (842-905° F.), and the final required temperature at which the catalyst requires replacement at end-of-run is from about 480 to about 520° C. (896-968° F.).

The process disclosed herein is based on the discovery that increasing the water environment surrounding the dehydrogenation catalyst after the catalyst has deactivated somewhat can significantly increase the length of the run or the effective life of the catalyst. Initially, the process described herein is operated with a sum of a concentration of water and an equivalent concentration of water precursors in the combined feed of less than 50 wt-ppm and preferably less than 10 wt-ppm based on the weight of the combined feed passed to the reaction zone. This relatively low concentration of water and water precursors can usually be achieved simply by not injecting or introducing water or water precursors into the combined feed or any of the streams that combine to form the combined feed. Even without injection or introduction of water or water precursors into these, one or more of these streams may contain water or water precursors. For example, the hydrocarbon feed or a stream of unconverted dehydrogenatable hydrocarbons may contain a low or trace concentration of water or water precursors. Preferably the hydrocarbon feed stream is as dry as possible and there is no introduction of water or water precursor into the hydrocarbon feed. The gaseous recycle stream may also contain water and may in fact contribute more water to the combined feed than the hydrocarbon feed. Water is present in the recycle gas results when the reactor effluent contains water since phase separating the reaction effluent concentrates a majority of the water in the gaseous stream. The separation conditions and the ratio of the gaseous recycle stream to the gaseous net stream from the separator have a large influence on the amount of water carried in the gaseous recycle stream. If any of these streams contains an excessive amount of water or water precursors such that the initial maximum sum of 50 wt-ppm or preferably 10 wt-ppm is exceeded, a person of ordinary skill in the art can use known methods such as drying, adsorption, or stripping, for removing water or water precursors from each stream as needed.

In order to increase the concentration of water, water precursors, or both in the combined feed, water or water precursors may be injected or introduced into the combined feed itself, the hydrocarbon feed, the gaseous recycle stream, a stream of unconverted hydrocarbons, or any other stream that combines to form the combined feed. A person of ordinary skill in the art knows analytical techniques for measuring the content of water or water precursors in these streams.

When a combined feed containing water precursor is introduced into a dehydrogenation zone containing dehydrogenation catalyst at dehydrogenation conditions, the water precursor is rapidly converted to water. A water precursor is preferably any convenient oxygen-containing compound that performs according to the teachings contained herein. A water precursor in the hydrocarbon feed or the unconverted hydrocarbons may, for example, be any alcohol, aldehyde, epoxide, ketone, phenol or ether that has a molecular weight or boiling point within the range of molecular weights or boiling points of the hydrocarbons in the hydrocarbon feed. A water precursor in the gaseous recycle stream may be any low molecular weight alcohol or ether such as, for example, methanol, ethanol, propanol ethyl ether, methyl tert-butyl ether and isopropyl ether.

The combined feed has a concentration of water that is expressed herein in units of wt-ppm of water based on the weight of the combined feed. The combined feed has a concentration of water precursors that is referred to herein as an equivalent concentration of water precursors. The equivalent concentration of a water precursor is the concentration of water that would result from the water precursor converting to water in the combined feed. A person of ordinary skill in the art can compute the equivalent concentration of a water precursor by multiplying the concentration of water precursor in a feed or stream by a factor equal to the amount of water that would be produced per water precursor converted. The concentration of water precursor in the combined feed is expressed herein in units of wt-ppm based on the weight of the combined feed. Therefore, the equivalent concentration of water precursor is computed by multiplying the concentration of water precursor in wt-ppm by a factor equal to the weight of water that would be produced per unit weight of water precursor converted. (The factor is 0.56 for methanol ($CH_3OH$) and 0.58 for ethylene glycol ($C_2H_4(OH)_2$).)

In one embodiment of the process disclosed herein, the water, water precursors, or both in the combined feed is increased when the temperature required to maintain an preselected initial conversion per pass of the dehydrogenatable hydrocarbon to the reactor increases by at least 2° C. (4° F.), by from 2 to 8° C. (4 to 14° F.), or by at least 15° C. (27° F.). The actual reaction temperature may be higher than the initial temperature required to maintain the preselected conversion by the same amounts when the increase occurs. The increase results in the sum of the concentration of water and the equivalent concentration of a water precursor being at least 200 wt-ppm, or from 200 to about 10000 wt-ppm, based on the weight of the combined feed passed to the reaction zone. As an example of the increase in the length of the run in terms of days on stream, an optimized unit may run about ninety days per catalyst loading. If the increase in water or water precursors is started on the second day, the run may be extended about nine days. If the increase is started on the ninetieth day, the run may be extended about sixty days.

The reaction temperature or the required temperature is generally measured at the inlet of the combined feed to the reaction zone. The dehydrogenation reactions tend to be endothermic, which typically causes a temperature drop across the reaction zone. If heat is supplied to the reaction zone, as described for instance in U.S. Pat. No. 6,118,038, the temperature drop may be reduced significantly compared to that in an adiabatic reaction zone. In any event, a suitable location in or at the reaction zone can be selected for measuring the reaction or required temperature that is indicative of the change in temperature that is made as a result of catalyst deactivation.

The difference between the initial temperature required to maintain a preselected conversion per pass and the temperature at which the catalyst must be replaced is typically from 15 to 30° C. (27-54° F.). This temperature difference is often the difference between the start-of-run temperature (SORT) and end-of-run temperature (EORT). In this embodiment, the increase in the water, water precursors, or both to the reaction zone may be made after the temperature required to maintain the preselected conversion per pass increases by at least 2° C. (4° F.) but by less than 40%, less than 30%, or less than 20% of the difference between the initial temperature required to maintain a preselected conversion per pass and the temperature at which the catalyst must be replaced. That is, the increase is made after the temperature required to maintain the preselected conversion per pass increases by at least 2° C. (4° F.) but before the temperature increase is 6 to 12° C. (11 to 22° F.), or when the temperature increase is less than 5 to 9° C. (9 to 16° F.).

After the increase in water, water precursors, or both in the combined feed to the reaction zone, the sum of the concentration of water and the equivalent concentration of water precursors in the combined feed is preferably maintained not less than the sum prior to the increase. In this embodiment, the sum can be further increased after an initial increase. However, once the sum of the concentration of water and the equivalent concentration of water precursors in the combined feed is relatively high, such as above 2000 wt-ppm or above 4000 wt-ppm based on the weight of the combined feed passed to the reaction zone, further increases in the sum may effect relatively little further improvement in the duration of the run or the effective life of the catalyst. Thus, in some cases it may be preferable to not raise the sum of the water concentration and the equivalent concentration of water precursors above the sum that is obtained as a result of an initial increase in the sum.

In practicing the process disclosed herein, the conversion per pass of feed paraffins to monoolefinic product increases, often dramatically by several molar percentage points, after the increase in water or water precursors. Although high conversions per pass appear to be beneficial, they often lead to undesired consequences, such as increases in side reactions and undesirable byproducts. High conversions per pass can create a sudden need for storage for the product olefins when the production of olefins in the dehydrogenation unit exceeds the capacity of downstream units to process the olefins. Therefore, it is often desirable in commercial practice to maintain the paraffin feed rate, the conversion per pass, and the olefin production rate substantially constant. Accordingly, in practicing this embodiment of the process disclosed herein, the inlet temperature of the dehydrogenation reaction zone may be decreased after the increase in water or water precursors. The required decrease in inlet temperature to maintain the preselected conversion per pass can be at least 2° C. (4° F.), from 2 to 8° C. (4 to 14° F.), at least 10° C. (18° F.), at least 15° C. (27° F.) or from 15 to 30° C. (27 to 54° F.). However, the extent that the temperature is decreased depends on several factors, including the catalyst, the reactor inlet temperature when the water or water precursors is increased, and the rate at which the water or water precursors are introduced.

The optimum conversion per pass of the process may be less than the maximum possible conversion per pass at any given catalyst life. Thus, it is possible to operate the process to obtain a number of different conversions per pass as the catalyst ages and as the temperature required to maintain the initial conversion per pass increases. However, it is preferable to operate the process at the maximum possible conversion per pass for a given catalyst life.

In another embodiment of the process disclosed herein, after the conversion per pass of the dehydrogenatable hydrocarbon through the reaction zone has decreased by at least 0.1, at least 0.5, or at least 1.0 molar percentage points, the sum of the concentration of water and the equivalent concentration of water precursors in the combined feed is increased to at least 100 wt-ppm based on the combined feed passed to the reaction zone. As the catalyst ages in this embodiment, the temperature of the reaction zone is preferably either not increased or maintained substantially constant. As used herein, maintaining the temperature of the reaction zone substantially constant means that the reaction temperature is changed by less than 2° C. (4° F.). This can improve the average selectivity over the duration of the run compared to a run in which higher reaction temperatures are used or a run in which the reaction temperature is increased throughout the run to maintain the initial preselected conversion. Preferably in this embodiment, the initial preselected conversion per pass is maintained during the run by increasing the sum of the concentration of water and the equivalent concentration of water precursors.

Accordingly, in this embodiment the sum of the concentration of water and the equivalent concentration of water precursors is increased from less than 50 wt-ppm and preferably less than 10 wt-ppm based on a decline in the conversion per pass of the process. For example, when the sum of the concentration of water and equivalent concentration of water precursors is less than 50 wt-ppm and preferably less than 10 wt-ppm, the dehydrogenation conditions result in an initial conversion per pass of, say, 10.0 mol-%. Then, after the conversion per pass of the process drops by at least 0.1 or at least 0.5 molar percentage points below the initial conversion per pass, the sum of the concentration of water and the equivalent concentration of water precursors is raised from less than 50 wt-ppm and preferably less than 10 wt-ppm to a higher sum of up to about 10000 wt-ppm, from 100 to about 10000 wt-ppm, from about 100 to about 300 wt-ppm, based on the weight of the combined feed passed to the reaction zone. This higher sum is referred to herein as the second sum and can result in an improvement to a higher conversion per pass, referred to herein as the second conversion per pass. Ideally, this second conversion per pass is as high as the initial conversion per pass, however it may be from 0.1 to about 5.0 molar percentage points, more commonly from about 0.1 to about 1.0 molar percentage points, below the initial conversion per pass. As the catalyst ages and the conversion per pass declines by a minimum of 0.1 or 0.5 molar percentage points below the second conversion per pass, the sum of the concentration of water and the equivalent concentration of water precursors is then raised from the second sum to what is referred to herein as the third sum of up to about 10000 wt-ppm, from 100 to about 10000 wt-ppm, or from about 300 to about 1000 wt-ppm, based on the weight of the combined feed passed to the reaction zone. Again, this increase may result in an improvement to a higher conversion per pass, referred to herein as the third conversion per pass. Preferably, the difference between the initial and third conversions per pass is small, but it may be between 0 and about 5.0 molar percentage points, more commonly from about 0.1 to about 1.0 molar percentage points. As the catalyst ages yet further and the conversion per pass drops again by at least 0.1 or at least 0.5 molar percentage points below the third conversion per pass, the sum of the concentration of water and the equivalent concentration of water precursors is raised from the third sum to a higher sum of up to about 10000 wt-ppm, from 100 to about 10000 wt-ppm, or from about 1000 to about 4000 wt-ppm, based on the weight of the combined feed passed to the reaction zone. This sequence of increasing the sum of the concentrations of water and water precursors in response to decreases in conversion per pass can be continued until the conversion per pass drops to such a low level that the process is no longer profitable or useful or until an upper limit is reached on the concentration of water or water precursors. Also, once the sum of the concentration of water and the equivalent concentration of water precursors in the combined feed is relatively high, further increases in the sum may have a diminishing effect on maintaining the conversion. The upper limit on the concentration of water or water precursors may be about 4000, about 10000, or from about 4000 to about 10000 wt-ppm, based on the weight of the combined feed to the reaction zone, or higher. After this upper limit is reached, if the reaction temperature is less than the EORT, the reaction temperature can be increased to the EORT in order to extend the duration of the run.

In this embodiment, the frequency, size, and/or the number of the changes in the sum of the concentration of water and equivalent concentration of water precursors can be chosen as needed to achieve a desired processing objective. In a preferred embodiment to maintain the conversion per pass close to the initial conversion per pass, each increase in the sum of the concentration of water and equivalent concentration of water precursors is relatively small and the increases are relatively frequent. For example, each increase may be in the range of from about 1 to about 1000 wt-ppm or from about 100 to about 300 wt-ppm based on the weight of the combined feed passed to the reaction zone. Such increases could be made as soon as the conversion per pass drops by at least 0.1, at least 0.5, or at least 1.0 molar percentage points. The increases are continued until the end of the run or until the previously-mentioned upper limit on the concentration of water or water precursors is reached.

The cause of the decrease in the conversion per pass of the dehydrogenatable hydrocarbon through the reaction zone can be any cause that results in a decrease in the conversion per pass, including but not limited to catalyst deactivation, catalyst aging, or a decrease in the temperature of the reaction zone. For example, the cause can be an intentional decrease in the temperature of the reaction zone by at least 2° C. (4° F.), from 2 to 8° C. (4 to 14° F.), at least 10° C. (18° F.), at least 15° C. (27° F.) or from 15 to 30° C. (27 to 54° F.).

The increase in water, water precursors, or both in the combined feed may occur simultaneously with other changes in the process. For example, the increase may occur after the selectivity at the preselected conversion per pass of the paraffinic hydrocarbon to the reactor decreases by a specified amount of, for instance, at least 1 molar percentage point. Selectivity is defined as the moles of monoolefins produced divided by the moles of feed paraffins that are converted, and as the catalyst ages the selectivity tends to decrease. The increase may also be made before a certain percentage, say 40%, 30%, or 20%, of the paraffins that may be processed before the catalyst requires replacement have passed through the reaction zone.

The period of time over which the increase in water or water precursors to the reaction zone occurs is believed to be not critical to the success of the process disclosed herein. Typically, the time for a change in the sum of the concentration of water and the equivalent concentration of water precursors is relatively short and may occur, for instance, as a step change over 10 or less seconds or less. Alternatively, the water or water precursors can be ramped up over a period of minutes or hours.

Other ways of practicing the process disclosed herein include maintaining the concentration of water at less than 5 wt-ppm and preferably less than 2 wt-ppm in the fresh hydrocarbon feed, or at less than 70 wt-ppm and preferably less than 40 wt-ppm in the combined feed, during an initial period of preferably at least one-half (50%) and more preferably at least 60% of the catalyst life has elapsed. During this initial period, water is not injected into the fresh hydrocarbon feed and water is prevented from mixing with the fresh hydrocarbon feed. After the initial period of preferably at least one-half (50%) and more preferably at least 60% of the catalyst life has elapsed, these other ways of practicing the process disclosed herein further include injecting water into the fresh hydrocarbon feed and maintaining the concentration of water at 30 to 1900 wt-ppm and preferably at 30 or 60 to 1500 wt-ppm in the fresh hydrocarbon feed, or at 200 to 6200 wt-ppm and preferably at 200 or 500 to 6200 wt-ppm in the combined feed. Once water injection is started, the concentration of water can be maintained constant or be increased gradually.

The dehydrogenatable hydrocarbons may be admixed with a diluent material before or while flowing through the reaction zone. The diluent material may be hydrogen, steam, methane, ethane, propane, butane, pentane, hexane, carbon dioxide, nitrogen, argon and the like or a mixture thereof. When hydrogen is the diluent, the hydrogen to hydrocarbon mole ratio is from about 0.1:1 to about 40:1, preferably from about 1:1 to about 10:1. The diluent will typically be separated from the reaction zone effluent and recycled to the reaction zone. Hydrogen or hydrocarbons having from 2 to 6 carbon atoms formed as byproducts in the reaction zone can be diluent.

Dehydrogenation conditions include a temperature of from about 400° C. to about 900° C., a pressure of from about 1 to about 1013 kPa and a liquid hourly space velocity (LHSV) of from about 0.1 to about 100 $hr^{-1}$. As used herein, the abbreviation "LHSV" means liquid hourly space velocity, which is defined as the volumetric flow rate of liquid per hour divided by the catalyst volume, where the liquid volume and the catalyst volume are in the same volumetric units. In general for paraffins, the lower the molecular weight, the higher is the temperature required for comparable conversion per pass. The pressure in the dehydrogenation zone is maintained as low as practicable, consistent with equipment limitations, to maximize the chemical equilibrium advantages.

In practicing the process disclosed herein, dehydrogenatable hydrocarbons are contacted with a dehydrogenation catalyst in a dehydrogenation zone maintained at dehydrogenation conditions. This contacting can be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then flowed into the dehydrogenation zone containing a fixed bed of the catalyst. The dehydrogenation zone may itself comprise one or more separate reaction zones with heating means there between to ensure that the desired reaction temperature can be maintained at the entrance to each reaction zone, but preferably the reaction zone is a single reactor. The hydrocarbon may be contacted with the catalyst bed in either upward, downward or radial flow fashion. The reaction zone may be an arrangement that provides indirect heat exchange, as described, for instance, in U.S. Pat. No. 6,118,038. Radial flow of the hydrocarbon through the catalyst bed is preferred. The hydrocarbon may be in the liquid phase, a mixed vapor-liquid phase or the vapor phase when it contacts the catalyst. Preferably, it is in the vapor phase.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The following examples are presented in illustration of the process disclosed herein and are not intended as limitations on the generally broad scope of the invention as set out in the appended claims.

EXAMPLE 1

Catalysts A, B, and C were dehydrogenation catalysts, each comprised a layered composition having an inner core and an outer layer bonded to the inner core. The properties of catalysts A, B, and C are in Table 1. Catalysts A, B, and C contained platinum and tin distributed uniformly on the outer layer. Catalyst D was a dehydrogenation catalyst containing platinum, tin, and lithium distributed uniformly on a gamma alumina support, and not a layered composition. Based on the weight of the catalyst, catalyst D contained 0.4 wt-% platinum, 0.5 wt-% tin, 0.6 wt-% lithium, and 0.4 wt-% indium. The atomic ratio of platinum to tin in catalyst D was 0.49.

TABLE 1

| Catalyst | A | B | C |
|---|---|---|---|
| Core | Cordierite | Cordierite | Cordierite |
| Core Diameter, mm | 1.80 | 1.76 | 1.68 |
| Layer | Gamma alumina | Gamma alumina | Gamma alumina |
| Layer Thickness, micron | 100 | 100 | 60 |
| Platinum, wt-% of catalyst | 0.16 | 0.16 | 0.43 |
| Tin, wt-% of catalyst | 0.13 | 0.13 | 0.32 |
| Lithium, wt-% of catalyst | 0.20 | 0.21 | 0.14 |
| Platinum/Tin Ratio, atomic | 0.74 | 0.74 | 0.83 |

The catalysts were tested for dehydrogenation activity in a laboratory scale plant. Catalyst was placed in a reactor and a hydrocarbon feed composed of 8.8-9.3 wt-% $n-C_{10}$, 40.0-41.8 wt-% $n-C_{11}$, 38.6 wt-% $n-C_{12}$, 8.6-10.8 wt-% $n-C_{13}$, 0.3-0.8 wt-% $n-C_{14}$ and 1-1.4 wt-% non-normals was flowed over the catalyst under a pressure of 138 kpa(g) (20 psi(g)), a $H_2$:hydrocarbon molar ratio of 4:1, and a liquid hourly space velocity (LHSV) of 28 $hr^{-1}$. The total normal olefin concentration in the product (% TNO) was maintained at 15 wt-% by adjusting the reactor inlet temperature. The conversion was stable and in the range of from 16 to 19%. Hydrogen and hydrocarbon feed were combined upstream of the reactor to form a combined feed, and the combined feed was vaporized prior to entering the reactor. Without any water injection, the concentration of water in the combined feed was less than 1 wt-ppm based on the weight of the combined feed. Catalysts were tested with and without water injection into the combined feed.

Tables 2-5 present the starting times for water injection, the concentrations of water based on the weight of the combined feed after injection began, and the improvements in run duration resulting from the injection.

EXAMPLE 2

Catalyst A was tested following the procedure in Example 1 in eight runs (Runs 2A to 2H), and water was injected into the combined feed during seven of the eight runs. Table 2 presents the test conditions and results for the runs. The start-of-run temperatures (SORTs) for the eight runs were within a range of 2° C. (4° F.), and the differences between the SORTs and the end-of-run temperatures (EORTs) were within a range of 2° C. (3° F.) for all eight runs except one. However, the variations in SORTs and in the differences between SORT and EORT did not have a significant effect on the improvements reported in Table 2, except as described below. Once water injection was started in runs 2B, 2D, and 2G, approximately 6000 wt-ppm water based on the weight of the combined feed was injected for varying periods of time, but these increases also did not have a significant effect on the improvements reported in Table 2. Shortly after water injection began after the start of a run, the reactor inlet temperature was lowered by from 2 to 17° C. (4 to 30° F.) depending on the run to maintain the % TNO at 15 wt-%. Thereafter, as the catalyst continued to age, the reactor inlet temperature was increased to maintain the % TNO at 15 wt-%.

Run 2A was a comparative run which had continuous 2000 wt-ppm water injection during the entire run. Slightly postponing the start of injection until only 2° C. (3-4° F.) of catalyst deactivation had occurred after the start of the run improved the run duration by 18% (Run 2B) and 11% (Run 2C). Further postponement until the reactor inlet temperature was about 10-11° C. (18-20° F.) above SORT increased the improvement to from 23% to 72% (Runs 2D, 2E, and 2F). The improvement in Run 2D's duration would have been significantly greater but for the fact that Run 2D ended earlier than the other seven runs and the difference between SORT and EORT for Run 2D was about one-fourth to one-third less than those of the other seven runs. Nevertheless, in Runs 2D, 2E, and 2F, the higher the water injection, the greater is the improvement in run duration. Run 2G, in which the start of water injection was postponed until EORT had been reached, had the greatest improvement (82%) of all eight runs and more than triple the improvement of Run 2H, which had no water injection. The approximately 6000 wt-ppm water injection in Run 2G occurred throughout the final 8° C. (15° F.) of catalyst deactivation at end of the run. Neither this relatively long increase to approximately 6000 wt-ppm nor the much shorter approximately 6000 wt-ppm surges in Runs 2B and 2D improved the durations of the run in which each occurred.

EXAMPLE 3

Catalyst B was tested twice according to the procedure in Example 1, and water was injected into the combined feed during both runs (Runs 3A and 3B). Table 3 presents the testing conditions and the resulting improvements. The SORTs for the runs were within 2° C. (3° F.), as were the differences between the SORTs and EORTs.

TABLE 2

|  | Start of Water Injection | | | Increase in Run Duration |
|---|---|---|---|---|
|  | Temperature - SORT | Time on Stream, | Water, | over Run 2A, |
| Run | °C. (°F.) | % of (EORT - SORT) | % of Run Duration | wt-ppm | % of Run 2A Duration |
| 2A | 0 (0) | 0 | 0 | 2000 | NA |
| 2B | 2 (4) | 12 | 16 | 200 | 18 |
| 2C | 2 (3) | 9 | 17 | 2000 | 11 |
| 2D | 11 (19) | 86 | 75 | 200 | 23 |
| 2E | 11 (20) | 67 | 63 | 2000 | 47 |
| 2F | 10 (18) | 58 | 53 | 4000 | 72 |
| 2G | 18 (32) | 100 | 66 | 4000 | 82 |
| 2H | NA | NA | NA | NA | 25 |

TABLE 3

|  | Start of Water Injection | | | Increase in Run Duration |
|---|---|---|---|---|
|  | Temperature - SORT | Time on Stream, | Water, | over Run 3A, |
| Run | °C. (°F.) | % of (EORT - SORT) | % of Run Duration | wt-ppm | % of Run 3A Duration |
| 3A | 0 (0) | 0 | 0 | 2000 | NA |
| 3B* | 17 (31) | 100 | 79 | 4000 | 69 |
| 3B** | NA | NA | NA | NA | 34 |

*Entire run.
**Until water injection started.

Run 3A was a comparative run which had continuous 2000 wt-ppm water injection during the entire run. In Run 3B, the start of injection was postponed until EORT had been reached. Without water injection the run duration improved by only 34%. Shortly after water injection began, the reactor inlet temperature was lowered by from 16° C. (29° F.) to maintain the % TNO at 15 wt-%. Subsequently the reactor inlet temperature was increased to maintain the % TNO at 15 wt-% as the catalyst aged. When the reactor inlet temperature had been raised to EORT a second time, the duration of Run 3B had improved by 69%, which was more than double the improvement that had been attained without water injection.

EXAMPLE 4

Catalyst C was tested according to the procedure in Example 1. Table 4 presents the test conditions and results of the run (Run 4). After water injection began, the reactor inlet temperature was first lowered by 9° C. (16° F.) and then subsequently increased, to maintain the % TNO at 15 wt-%. Starting water injection when EORT was reached improved the duration of Run 4 by 51%.

Run 5A was a comparative run which had 2000 wt-ppm water injection continuously throughout the entire run. By postponing the start of injection until EORT had been reached in Run 5B, the duration of Run 5B improved by 53%, which was nearly than triple the improvement (18%) achieved in Run 5B before water was injected.

EXAMPLE 6

Catalyst D was tested according to the procedure in Example 1. A temperature was chosen for the run (Run 6) to be the basis (BASE temperature) from which point catalyst deactivation, time on stream, and run duration were measured. The BASE temperature for Run 6 was the same as the BASE temperature for Runs 5A and 5B. The SORT was within 3° C. (5° F.) of those in Example 5, as was the difference between the SORT and EORT. However, the variations in SORTs and in the differences between SORT and EORT did not have a significant effect on the improvements reported in Table 6. Water was injected continuously throughout the entire run. Initially the water injection was 100 wt-ppm based on the weight of the combined feed. The reactor inlet tem-

TABLE 4

| | Start of Water Injection | | | Increase in |
| --- | --- | --- | --- | --- |
| Run | Temperature - SORT | Time on Stream, | Water, | Run Duration |
| | °C. (°F.) | % of (EORT - SORT) | % of Run Duration | wt-ppm | over BASE, % of BASE |
| 4* | 13 (23) | 100 | 79 | 4000 | 51 |
| 4** | NA | NA | NA | NA | BASE |

*Entire run.
**Until water injection started.

EXAMPLE 5

Catalyst D was tested twice according to the procedure in Example 1. Table 5 presents the test conditions and results. A temperature was chosen for the runs (Runs 5A and 5B) to be the basis (BASE temperature) from which point catalyst deactivation, time on stream, and run duration were measured. The BASE temperature for the runs was within 0.5° C. (1° F.) of the SORTs, as were the differences between the BASE temperature and EORTs. After water injection began in Run 5B, the reactor inlet temperature was lowered by from 11° C. (20° F.) to maintain the % TNO at 15 wt-%.

perature was adjusted to maintain the % TNO at 15 wt-% until the reactor inlet temperature was 12° C. (22° F.) above the BASE temperature, the difference between the reactor inlet temperature and the BASE temperature was 82% of the difference between EORT and the BASE temperature, and the time on stream was 81% of what would be the duration of Run 6. Water injection was then increased to 4000 wt-ppm based on the weight of the combined feed, and the reactor inlet temperature was lowered by from 6° C. (1° F.) to maintain the % TNO at 15 wt-%. Subsequently, the reactor inlet temperature was increased to maintain the % TNO at 15 wt-% until

TABLE 5

| | Start of Water Injection | | | Increase in Run Duration |
| --- | --- | --- | --- | --- |
| Run | Temperature - BASE | Time on Stream, | Water, | over Run 5A, |
| | °C. (°F.) | % of (EORT - BASE) | % of Run Duration*** | wt-ppm | % of Run 5A Duration*** |
| 5A | 0 (0) | 0 | 0 | 2000 | NA |
| 5B* | 14 (27) | 100 | 77 | 4000 | 53 |
| 5B** | NA | NA | NA | NA | 18 |

*Entire run.
**Until water injection started.
***Time on stream and run duration were measured from the point when the temperature was the BASE temperature.

EORT was reached again, at which time the duration of Run 6 was 47% longer than that of Run 5A.

TABLE 6

| Run | Start of Water Injection Temperature - BASE °C. (° F.) | Start of Water Injection % of (EORT - BASE) | Time on Stream, % of Run Duration*** | Water, wt-ppm | Increase in Run Duration over Run 5A, % of Run 5A Duration*** |
|---|---|---|---|---|---|
| 6* | 12 (22) | 82 | 81 | 4000 | 47 |
| 6** | 0 (0) | 0 | 0 | 100 | 18 |

*Entire run.
**Until water injection increased.
***Time on stream and run duration were measured from the point when the temperature was the BASE temperature.

Therefore, the duration of the run using Catalyst D with a delay in the start of water injection (Run 5B) was improved by 6 percentage points over that obtained when water was injected continuously first at 100 wt-ppm and then at 4000 wt-ppm (Run 6). Postponing the start of water injection to both layered and non-layered compositions resulted in a much greater benefit over continuously injecting water at a constant 2000 wt-ppm.

EXAMPLE 7

This is a prophetic example. Catalyst A is tested following the procedure in Runs 2A, 2G, and 2H (Runs 7A to 7C), and water is injected into the combined feed during two of the runs. The conversion is 8%. Table 7 presents the test conditions and results for the runs.

TABLE 7

| Run | Start of Water Injection Temperature - BASE °C. (° F.) | Start of Water Injection % of (EORT - BASE) | Time on Stream, % of Run Duration | Water, wt-ppm | Increase in Run Duration over Run 7A, % of Run 7A Duration |
|---|---|---|---|---|---|
| 7A | 0 (0) | 0 | 0 | 2000 | NA |
| 7B | 18 (32) | 100 | 57 | 4000 | 75 |
| 7C | NA | NA | NA | NA | 25 |

Run 7A is a comparative run which has continuous 2000 wt-ppm water injection. Postponing the start of water injection until EORT is reached improves the run duration by 75% (Run 7B) and triples the improvement of Run 7C, which has no water injection.

EXAMPLE 8

This is a prophetic example. Catalyst A is tested following the procedure in Example 1, except that the total normal olefin concentration in the product (% TNO) is maintained at 15 wt-% by increasing the water injection and without adjusting the reactor inlet temperature. The conversion is stable and in the range of 16 to 17%. Initially there is no water injection. Without any water injection, the concentration of water in the combined feed is less than 1 wt-ppm based on the weight of the combined feed. The concentration of water based on the weight of the combined feed is increased first to 100 wt-ppm and then in increments to 4000 wt-ppm to maintain the % TNO at 15 wt-%. Then the reactor inlet temperature is increased from the SORT to the EORT, which temperatures are the same as in Run 2A. The postponement in raising the reactor inlet temperature keeps the average reactor inlet temperature over the duration of the run less than that in Run 2A. The duration of the run is not less than that of Run 2A, and the average selectivity over the duration of the run is greater than that in Run 2A

What is claimed is:

1. A process for the catalytic dehydrogenation of a paraffinic hydrocarbon having from 5 to 20 carbon atoms per molecule in a reaction zone at a temperature required to effect a conversion per pass of the paraffinic hydrocarbon through the reaction zone, the process comprising:
  a) passing a combined feed comprising the paraffinic hydrocarbon and any recycle streams to the reaction zone, the combined feed comprising the paraffinic hydrocarbon and any recycle streams together having a first water concentration and a first equivalent concentration of water precursors, the sum of the first water concentration and the first equivalent concentration being less than 10 wt-ppm based on the weight of the combined feed passed to the reaction zone, the reaction zone containing a dehydrogenation catalyst comprising a platinum group component and a promoter component supported on a carrier material, the temperature being a first temperature and the conversion per pass being a first conversion per pass; and
  b) increasing at least one of the water or the water precursors in the combined feed such that the combined feed has a second water concentration and a second equivalent concentration of water precursors, the sum of the second water concentration and the second equivalent concentration being at least 100 wt-ppm based on the weight of the combined feed passed to the reaction zone, after the conversion per pass is at least 0.1 molar percentage points less than the first conversion per pass, and maintaining the reaction zone at a temperature that is not more than or is substantially the same as the first temperature.

2. The process of claim 1 wherein the sum of the second water concentration and the second equivalent concentration is from 100 to about 10000 wt-ppm based on the weight of the combined feed passed to the reaction zone.

3. The process of claim 1 wherein the sum of the second water concentration and the second equivalent concentration is from 100 to about 300 wt-ppm based on the weight of the combined feed passed to the reaction zone.

4. The process of claim 1 further characterized in that in step b the reaction zone is maintained at a temperature that is substantially the same as the first temperature.

5. The process of claim 1 further characterized in that after said increasing of at least one of the water or the water precursors in the combined feed:
   c) increasing at least one of the water or the water precursors in the feed or recycle streams or both such that the combination of the feed and any recycle streams has a third water concentration and a third equivalent concentration of water precursors, the sum of the third water concentration and the third equivalent concentration being greater than the sum of the second water concentration and the second equivalent concentration.

6. The process of claim 5 wherein after said increasing of at least one of the water or the water precursors in step b the conversion per pass is a second conversion per pass and further characterized in that said increasing of at least one of the water or the water precursors in step c occurs after the conversion per pass is at least 0.1 molar percentage points below the second conversion per pass.

7. The process of claim 5 wherein the sum of the third water concentration and the third equivalent concentration is from about 300 to about 1000 wt-ppm based on the weight of the combined feed passed to the reaction zone.

8. The process of claim 5 further characterized in that in step c the reaction zone is maintained at a temperature that is substantially the same as the first temperature.

9. The process of claim 5 further characterized in that after said increasing of at least one of the water or the water precursors in step c:
   d) increasing at least one of the water or the water precursors in the feed or in any recycle stream or both such that the combination of feed plus recycle streams has a fourth water concentration and a fourth equivalent concentration of water precursors, the sum of the fourth water concentration and the fourth equivalent concentration being greater than the sum of the third water concentration and the third equivalent concentration.

10. The process of claim 9 wherein after said increasing of at least one of the water or the water precursors in step c the conversion per pass is a second conversion per pass and further characterized in said increasing of at least one of the water or the water precursors in step d occurs after the conversion per pass is at least 0.1 molar percentage points below the third conversion per pass.

11. The process of claim 9 wherein the sum of the fourth water concentration and the fourth equivalent concentration is from about 1000 to about 4000 wt-ppm based on the weight of the feed plus any recycle streams passed to the reaction zone.

12. The process of claim 9 further characterized in that in step c the reaction zone is at a temperature that is substantially the same as the first temperature.

13. The process of claim 1 wherein the platinum group component comprises a component selected from the group consisting of platinum, palladium, iridium, rhodium, osmium, ruthenium, and mixtures thereof and the promoter component comprises a component selected from the group consisting of tin, germanium, rhenium, gallium, bismuth, lead, indium, cerium, zinc, and mixtures thereof.

14. The process of claim 1 wherein the platinum group component comprises platinum and the promoter component comprises tin.

15. The process of claim 1 wherein the dehydrogenation catalyst comprises a modifier component comprising a component selected from the group consisting of an alkali metal, an alkaline earth metal, and mixtures thereof.

16. The process of claim 1 wherein the dehydrogenation catalyst comprises a layered composition comprising an inner core, an outer layer bonded to the inner core, the outer layer comprising the carrier material, the carrier material comprising a refractory inorganic oxide, the outer layer having a thickness of from about 40 to about 150 microns and having uniformly dispersed thereon the platinum group component and the promoter component.

17. The process of claim 1 wherein the dehydrogenation catalyst comprises catalyst particles, the platinum group component is surface-impregnated upon the catalyst particles such that the average concentration of the surface-impregnated platinum group component on the outside 200 micron layer of the catalyst particle is at least 2 times the concentration of the platinum group component in the 200 micron diameter center core of the catalyst particles.

18. The process of claim 1 wherein the dehydrogenation catalyst has an atomic ratio of platinum group component to promoter component of from about 0.05 to about 5.

19. The process of claim 1 wherein said increasing of at least one of the water or the water precursors in the feed or a recycle stream occurs after the conversion per pass is at least 0.5 molar percentage points less than the first conversion per pass.

20. The process of claim 1 wherein said increasing of at least one of the water or the water precursors in the combined feed occurs after the conversion per pass is at least 1.0 molar percentage points less than the first conversion per pass.

* * * * *